United States Patent
Kammerzell

(10) Patent No.: US 11,021,713 B2
(45) Date of Patent: Jun. 1, 2021

(54) ENGINEERED NUCLEASES TO GENERATE DELETION MUTANTS IN PLANTS

(71) Applicant: CARGILL, INCORPORATED, Wayzata, MN (US)

(72) Inventor: Meridith Kammerzell, Fort Collins, CO (US)

(73) Assignee: Cargill, incorporated, Wayzata, MN (US)

( * ) Notice: Subject to any disclaimer, the term of this patent is extended or adjusted under 35 U.S.C. 154(b) by 0 days.

(21) Appl. No.: 16/302,381

(22) PCT Filed: May 25, 2017

(86) PCT No.: PCT/US2017/034541
§ 371 (c)(1),
(2) Date: Nov. 16, 2018

(87) PCT Pub. No.: WO2017/205665
PCT Pub. Date: Nov. 30, 2017

(65) Prior Publication Data
US 2019/0185870 A1     Jun. 20, 2019

Related U.S. Application Data

(60) Provisional application No. 62/341,489, filed on May 25, 2016.

(51) Int. Cl.
*C12N 15/82* (2006.01)

(52) U.S. Cl.
CPC ..... *C12N 15/8247* (2013.01); *C12N 15/8213* (2013.01)

(58) Field of Classification Search
CPC ................ C12N 15/8247; C12N 15/8213
See application file for complete search history.

(56) References Cited

U.S. PATENT DOCUMENTS

2013/0031678 A1* 1/2013 Zheng ................. C12N 9/16
800/306

FOREIGN PATENT DOCUMENTS

| WO | 2006105946 A2 | 10/2006 | |
|---|---|---|---|
| WO | WO-2008037436 A1 * | 4/2008 | ......... C12N 15/8209 |
| WO | 2009007091 A2 | 1/2009 | |
| WO | 2011049627 A1 | 4/2011 | |
| WO | 2011075716 A1 | 6/2011 | |
| WO | 2015077661 A1 | 5/2015 | |
| WO | 2017205665 A1 | 11/2017 | |

OTHER PUBLICATIONS

You et al (Genome-wide Identification and Characterization of the Gene Families Controlling Fatty Acid Biosynthesis in Flax (*Linum usitatissimum* L). J Proteomics Bioinform 7: 310-326, 2014) (Year: 2014).*
Sun et al (Simultaneous over-expressing of an acyl-ACP thioesterase (FatB) and silencing of acyl-acyl carrier protein desaturase by artificial microRNAs increases saturated fatty acid levels in Brassica napus seeds. Plant Biotechnology Journal 12, pp. 624-637, 2014) (Year: 2014).*
Facciotti et al (Improved stearate phenotype in transgenic canola expressing a modified acyl-acyl carrier protein thioesterase. Nature Biotechnology 17:593-597, 1999) (Year: 1999).*
Hawkins et al (Characterization of acyl-ACP thioesterases of mangosteen (*Garcinia mangostana*) seed and high levels of stearate production in transgenic canola The Plant Journal 13: 743-752, 1998) (Year: 1998).*
Barker et al (Novel Insights into Seed Fatty Acid Synthesis and Modification Pathways from Genetic Diversity and Quantitative Trait Loci Analysis of the Brassica C Genome. Plant Physiology, vol. 144, pp. 1827-1842, 2007) (Year: 2007).*
Bonaventure, Gustavo , et al., "Disruption of the FATB Gene in *Arabidopsis* Demonstrates an Essential Role of Saturated Fatty Acids in Plant Growth", Plant Cell, American Society of Plant Biologists, vol. 15, No. 4. XP002517757, Apr. 1, 2003, 1020-1033.
Takami , et al., "De Novo Biosynthesis of Fatty Acids Plays Critical Roles in the Response of the Photosynthetic Machinery to Low Temperature in *Arabidopsis*", Plant and Cell Physiology, vol. 51, No. 8, XP55393534, Aug. 1, 2010. 1265-1275.

* cited by examiner

*Primary Examiner* — Ashley K Buran
*Assistant Examiner* — Wayne Zhong

(57) ABSTRACT

Methods are provided to mutate, in a targeted manner, the genome of a plant cell using a double stranded DNA break inducing enzyme. Also provided are plants, in particular *Brassica* plants that yield seeds producing oils having a reduced total saturated fatty acid content, and method for making such plants.

16 Claims, 8 Drawing Sheets
Specification includes a Sequence Listing.

ATGTCTCTCCATCTCCACTACCGGCTCTGTCAATTGTAACAGATCCCATCCTCCTTTTTAGATCTACAAATAATTAACT
TTCTCATCATCTCTCTTATGTGTGGCTTTGATTTTGTTGCAGGTTGAAGAATCGAAGGGTGGAGACGAACCAATGG
AGCGATGTGGTGATGACAGAGGAAGAGGGGATTCAGTTTCTAATGGTGGACGCTCGTCACAGATCTTTTGCAGGT
TAGATTGTAGATAGTTAAAACTATGTATGAATTTTGATTGGTCAATATTTAAAAAAAAAATAACTTTGTTGTTGGTT
TGATGTATGTGAGGAGGTGCGATGTAATCAGTTTCAGAGCGTTGCATTTTCGACTGATGGGATTGCGACAACACCT
ACCATGAGGAAACTGAATCTCATTTGGGTCACTTCGAGAATGCACATTGAGATCTACAGATATCCAGCTTGGTATT
GTTTTTTTCATTTTTGCTCTGTATGTTTGATGACAACAAATGGATTGAATTTTTGAAAATTTTGGTTACAGGGGTGAT
GTGGTTGAGATAGAGACATGGTGTCAGAGTGAAGGAAGGATCGGGACAAGGCGTGATTGGATTCTTAAGGACAT
TGCTAACGCTGAAGTCACTGGCTGTGCTACTAGGTTTCCTTCTCATCATTTTTTGCTTTCTCCATTGGTTTGTGCAA
TAGAATTAAATTTTCTTATGTTAAAGATATAACTTTCAGTTACTTGGATTTATGTTAAAGATATAATTTTCATTTCCG
AGCACTTGATGTTCTGTCTTAAAGAACCCAGGTAAAAGGAACTTTGTGTCCAGGTCAATGCAATGCTTGCTGGTCA
ATCATATCGTTATATTCATGAAATGCCCACTACTATGTTTATGTATATCTTTGTAGATTAGCATTTCCTGTGGAGGA
AAATAACAGAAGCTTGAAGAAAATCCCCACACTCGAAGATCTAGCTAAGTACTCAATCATTGGACTAAAGGTATAA
AATAGAAAATAATATTCTTTGTAGGAATCAACATTCCTAGAGGACTTTATAATCATGTTTCTTTGCAGCCAAGACG
AGCTGATCTCGACATGAACCATCATGTCAATAATTTCACCTATATTGGATGGATTCTTGAGGTTAGTGTCATCATCA
GGTTCTTTTTAAAATAATAACTTCAGTAATCACCATATGACTTTGTTTTCTGATATTGTCAGAGCATACTCAAGAGAT
TGTAGACACGCATGAACTTTGGATTACAGACGAGAATGTCAGCAAGACGATGTGGTGGATTCACTCACCACCTCA
AGAATGGCTCTGCAACATCAGGCACACAAAGCCACAACGATAGCCAGTTCTTATCTGGAGATGGTCAGGAGATC
AACTGTGGGACAACCCTGTGGAGAAAGAAGCCCTCCAGATAGACAATCCCTAAGCCATTACGAGTCAAGGACCAA
TCATTTTCACATAAACCTCTTTGCTTATTTGATTAAACAAGTTACATGACTGATAACAGATTCTGCCTATTACAAAGT
CTCATAAATTTCAAATAATGTGAGTAAATAAATAGAAAACAGAGAATTGG (SEQ ID NO:1)

FIG. 1

GGATAAATGTCTTCTCCATCTCCTGTTCCCATATAAGAAAACCTGGTTTGAGTCCTCTGCGGGCGGCTGTATCTGCT
GATCAAGAAAGTGTGATTCGAGCAGAACAAGGTTTGGACACACTCGCGGGTCGGCTCCGGTTGGGTAGCTTGAC
GGAGGATGGTTTATCGTATAAAGAGAAGTTCATAGTCAGATCCCACGAAGTGCAGAGTAACAAAACCGCTACGGT
CCAAACCATTGCCAATCTTTTGCAGGTTAGATTGTAGTTTGTTTAAAACTATGTATGAATCTTGATTGGTCAATATTT
TAAAAATAAGAATTTTATTTTGTTGGTTTGATGTATTTAGGAGGTGGGATGTAATCAGTTTCAGAGCGTTGGATTTT
CGACTGATGGGTTTGCGACAACACCTACCATGAGGAAACTGAATCTCATTTGGGTCACTTCGAGAATGCACATTGG
GATTTACAAATATCCAGCTTGGTATTTTTTTCTTCTGCTGTGTATGTTTTGATGACACAACAAATGAGCAGAGATTTT
GAAATTTTTGGTTACAGGGGTGATGTGGTTGAGATAGAGACATGGTGTCAGAGTGAAGGAAGGATCGGGACAAG
GCATGATTGGATTCTTAAGGATGTTGCTAACGGTGAAGTCACTGGCCGTACTACTAGGTTTCCCTCTCATCA (SEQ
ID NO:2)

FIG. 2A

GGATAAATGTCTTCTCCATCTCCTGTTCCCATATAAGAAAACCTGGTTTGAGTCCTCTGCGGGCGGCTGTATCTGCT
GATCAAGAAAGTGTGATTCGAGCAGAACAAGGTTTGGACACACTCGCGGGTCGGCTCCGGTTGGGTAGCTTGAC
GGAGGATGGTTTATCGTATAAAGAGAAGTTCATAGTCAGATCCCACGAAGTGCAGAGTAACAAAACCGCTACGGT
CCAAACCATTGCCAATCTTTTGCAGGTTAGATTGTAGTTTGTTTAAAACTATGTATGAATCTTGATTGGTCAATATTT
TAAAAATAAGAATTTTATTTTGTTGGTTTGATGTATTTAGGAGGTGGGATGTAATCAGTTTCAGAGCGTTGGATTTT
CGACTGATGGGTTTGCGACAACACCTACCATGAGGAAACTGAATCTCATTTGGGTCACTTCGAGAATGCACATTGG
GATTTACAAATATCCAGCTTGGTATTTTTTTCTTCTGCTGTGTATGTTTTGATGACACAACAAATGAGCAGAGATTTT
GAAATTTTTGGTTACAGGGGTGATGTGGT------------------
GTCAGAGTGAAGGAAGGATCGGGACAAGGCATGATTGGATTCTTAAGGATGTTGCTAACGGTGAAGTCACTGGC
CGTACTACTAGGTTTCCCTCTCATCA (SEQ ID NO:3)

FIG. 2B

```
            MEGANUCLEASE TARGET
AGGGGTGATGTGGTTGAGATAGAGACATGGTGTCAGAGTGAAGGAAGGATC
  G  D  V  V  E  I  E  T  W  C  Q  S  E  G  R  I

AGGGGTGATGTGGT---------------------GTCAGAGTGAAGGAAGGATC
```

FIG. 2C

GGATAAATGTCTTCTCCATCTCCTGTTCCCATATAAGAAAACCTGGTTTGAGTCCTCTGCGGGCGGCTGTATCTGCT
GATCAAGAAAGTGTGATTCGAGCAGAACAAGGTTTGGACACACTCGCGGGTCGGCTCCGGTTGGGTAGCTTGAC
GGAGGATGGTTTATCGTATAAAGAGAAGTTCATAGTCAGATCCCACGAAGTGCAGAGTAACAAAACCGCTACGGT
CCAAACCATTGCCAATCTTTTGCAGGTTAGATTGTAGTTTGTTTAAAACTATGTATGAATCTTGATTGGTCAATATTT
TAAAAATAAGAATTTTATTTTGTTGGTTTGATGTATTTAGGAGGTGGGATGTAATCAGTTTCAGAGCGTTGGATTTT
CGACTGATGGGTTTGCGACAACACCTACCATGAGGAAACTGAATCTCATTTGGGTCACTTCGAGAATGCACATTGA
GATTTACAAATATCCAGCTTGGTATTTTTTTTTTGCTGTGTATGTTTTGATGACACAACAAATGAGCAGAGATTTTG
AAATTTTGGTATAGGGGTGATGTGGTTGAGA------
CATGGTGTCAGAGTGAAGGAAGGATCGGGACAAGGCGTGATTGGATTCTTAAGGATCTTGCTAACGGTGAAGTC
ACTGGCCGTACTACTAGGTTTCCCTCTCATCA (SEQ ID NO:7)

FIG. 2D

| MEGANUCLEASE TARGET | | | | | | | | | | | | | | | | | |
|---|---|---|---|---|---|---|---|---|---|---|---|---|---|---|---|---|---|
| A|G|G|G|T|G|A|T|G|T|G|G|T|T|G|A|G|A|

AGGGTGATGTGGTTGAGAATAGAGACATGGTGTCAGAGTGAAGGAAGGATC
 G  D  V  V  E  I  E  T  W  C  Q  S  E  G  R  I

AGGGGTGATGTGGTTGAGA----------CATGGTGTCAGAGTGAAGGAAGGATC

FIG. 2E

TCAATCTTGATTGGTGGAATTTGTAAAGACAAGAACTTTGTTGGTTGGTTGATGTGTATATTATAGGAGGTGGGAT
GTAATCATGCGCAGAGCGTTGGATTCTCGACTGATGGGTTTGCGACAACACCGACAATGAGGAAACTGCATCTCA
TTTGGGTCACTGCGAGAATGCATATAGAGATCTACAAGTACCCTGCTTGGTATTTGGTTTCTGCTTCGTTTCTTTTTA
TCTATGTGTCTCTGTTTTGATGACAACTTAATGAGAGGAATCTTTTGGTTACAGGGGTGATGTGGTTGAGATAGAG
ACATGGTGTCAGAGTGAAGGAAGGATCGGGACTAGGCGTGATTGGATTCTTAAGGATGTTGCTACGGGTGAAGT
CACTGGCCGTGCTACAAGGTTTCCTTTTCATCATTTTTTTTTAGCTTCCTGGATTGGTTTGGACCTTTATGTTCCGTAT
TTAATGGTATTGTCGTGATTTGTTGTTTGAC (SEQ ID NO:9)

FIG. 3A

TCAATCTTGATTGGTGGAATTTGTAAAGACAAGAACTTTGTTGGTTGGTTGATGTGTATATTATAGGAGGTGGGAT
GTAATCATGCGCAGAGCGTTGGATTCTCGACTGATGGGTTTGCGACAACACCGACAATGAGGAAACTGCATCTCA
TTTGGGTCACTGCGAGAATGCATATAGAGATCTACAAGTACCCTGCTTGGTATTTGGTTTCTGCTTCGTTTCTTTTTA
TCTATGTGTCTCTGTTTTGATGACAACTTAATGAGAGGAATCTTTTGGTTACAGGGGTGATGTGGTTGAGA------
CATGGTGTCAGAGTGAAGGAAGGATCGGGACTAGGCGTGATTGGATTCTTAAGGATGTTGCTACGGGTGAAGTC
ACTGGCCGTGCTACAAGGTTTCCTTTTCATCATTTTTTTTTAGCTTCCTGGATTGGTTTGGACCTTTATGTTCCGTATT
TAATGGTATTGTCGTGATTTGTTGTTTGAC (SEQ ID NO: 10)

FIG. 3B

```
GTTACAGGGGTGATGTGGTTGAGATAGAGACATGGTGTCAGAGTGAAGGAAGGATC
  G  D  V  V  E  I  E  T  W  C  Q  S  E  G  R  I
         MEGANUCLEASE TARGET

GTTACAGGGGTGATGTGGTTGAGA----------CATGGTGTCAGAGTGAAGGAAGGATC
```

FIG. 3C

GATTTTCGACTGATGGGTTTGCAACAACACCTACCATGAGGAAACTGAATCTCATTTGGGTCACTTCGAGAATGCA
CATTGAGATTTACAAATATCCAGCTTGGTATTTTTTTTTTGCTGTGTATGTTTTGATGACACAACAAATGAGCAGAG
ATTTTGAAATTTTGGTATAGGGGTGATGTGGTTGAGATAGAGACATGGTGTCAGAGTGAAGGAAGGATCGGGAC
AAGGCGTGATTGGATTCTTAAGGATCTTGCTAACGGTGAAGTCACTGGCCGTGCTACTAGGTTTCCCTCTCATCATT
GTTAGCTTTCTCCATTGGTTTGTGCAATGGAATTAAATTTTCTTATGTTAAAGATATAATTTTCAGTTACTTGGATTT
ATGGGACTGTCATGATTTGTTGTACCTATGTTTGTGTTACTGTTTCAGCAAGTGGGTGATGATGAACCAAGACACA
AGACGGCTACAGAAAGTTTCTGATGATATCCGGGACGAGCACTTGATTT (SEQ ID NO:13)

FIG. 4A

GATTTTCGACTGATGGGTTTGCAACAACACCTACCATGAGGAAACTGAATCTCATTTGGGTCACTTCGAGAATGCA
CATTGAGATTTACAAATATCCAGCTTGGTATTTTTTTTTTGCTGTGTATGTTTTGATGACACAACAAATGAGCAGAG
ATTTTGAAATTTTGGTATAGGGGTGATGTGGTTGA--------------------
AGGAAGGATCGGGACAAGGCGTGATTGGATTCTTAAGGATCTTGCTAACGGTGAAGTCACTGGCCGTGCTACTAG
GTTTCCCTCTCATCATTGTTAGCTTTCTCCATTGGTTTGTGCAATGGAATTAAATTTTCTTATGTTAAAGATATAATTT
TCAGTTACTTGGATTTATGGGACTGTCATGATTTGTTGTACCTATGTTTGTGTTACTGTTTCAGCAAGTGGGTGATG
ATGAACCAAGACACAAGACGGCTACAGAAAGTTTCTGATGATATCCGGGACGAGCACTTGATTT (SEQ ID NO:14)

FIG. 4B

TATGAATGGAAAAAAGTATCAATCTTTGTAATTATGAATCTTGATTGGTCAATTGTGAAAGACAAGAACTTTGTTG
GTTGATTGATGTGTATATAGGAGGTGGGATGTAATCATGCTCAGAGCGTAGGATTCTCGACTGATGGGTTTGCGA
CAACACCTACCATGAGGAAATTGCATCTCATTTGGGTCACTGCCAGAATGCACATTGAGATCTACAAGTACCCTGC
TTGGTATTGGTTTCTGCTTCATCTGTCTATCTATCTAGATGTGTCTCTGTTTTGATGACAACTAACGAGGAATCTTTC
GGTTTACAGGGGTGATGTGGTTGAGATAGAGACATGGTGTCAGAGTGAAGGAAGGATCGGGACTAGGCGTGATT
GGATTCTTAAGGATGTTGCTACCGGTGAAGTCACTGGCCGTGCTACAAGGTTTCCTTTTCATCATTTTTTTAGCTTCC
GGGATTGGTTTGGGACCTTAATGTTCCGTATTTTATGGTGCTGTCCTGATTTGTTGTTTG (SEQ ID NO:18)

FIG. 5A

TATGAATGGAAAAAAGTATCAATCTTTGTAATTATGAATCTTGATTGGTCAATTGTGAAAGACAAGAACTTTGTTG
GTTGATTGATGTGTATATAGGAGGTGGGATGTAATCATGCTCAGAGCGTAGGATTCTCGACTGATGGGTTTGCGA
CAACACCTACCATGAGGAAATTGCATCTCATTTGGGTCACTGCCAGAATGCACATTGAGATCTACAAGTACCCTGC
TTGGTATTGGTTTCTGCTTCATCTGTCTATCTATCTAGATGTGTCTCTGTTTTGATGACAACTAACGAGGAATCTTTC
GGTTTACAGGGGTGATGTGGTTGA------------------------
AGGAAGGATCAGGACTAGGCGTGATTGGATTCTTAAGGATGTTGCTACCGGTGAAGTCACTGGCCGTGCTACAAG
GTTTCCTTTTCATCATTTTTTTAGCTTCCGGGATTGGTTTGGGACCTTAATGTTCCGTATTTTATGGTGCTGTCCTGAT
TTGTTGTTTG (SEQ ID NO 19)

FIG. 5B

SEQUENCE LISTING

```
<160> NUMBER OF SEQ ID NOS: 21

<210> SEQ ID NO 1
<211> LENGTH: 1582
<212> TYPE: DNA
<213> ORGANISM: Brassica napus

<400> SEQUENCE: 1
atgtctctcc atctccacta ccggctctgt caattgtaac agatcccatc ctcctttta      60 gatctacaaa taattaactt tctcatcatc tctcttatgt gtggctttga ttttgttgca    120
ggttgaagaa tcgaagggtg gagacgaacc aatggagcga tgtggtgatg acagaggaag    180 agggattca gtttctaatg gtggacgctc gtcacagatc ttttgcaggt tagattgtag    240
atagttaaaa ctatgtatga attttgattg gtcaatattt aaaaaaaaaa taactttgtt    300
gttggtttga tgtatgtgag gaggtgcgat gtaatcagtt tcagagcgtt gcattttcga    360
ctgatgggat tgcgacaaca cctaccatga ggaaactgaa tctcatttgg gtcacttcga    420
gaatgcacat tgagatctac agatatccag cttggtattg ttttttttcat ttttgctctg    480 tatgtttgat gacaacaaat ggattgaatt tttgaaaatt ttggttacag gggtgatgtg    540
gttgagatag agacatggtg tcagagtgaa ggaaggatcg ggacaaggcg tgattggatt    600
cttaaggaca ttgctaacgc tgaagtcact ggctgtgcta ctaggtttcc ttctcatcat    660
ttttttgctt tctccattgg tttgtgcaat agaattaaat tttcttatgt taaagatata    720
actttcagtt acttggattt atgttaaaga tataattttc atttccgagc acttgatgtt    780
ctgtcttaaa gaacccaggt aaaaggaact ttgtgtccag gtcaatgcaa tgcttgctgg    840
tcaatcatat cgttatattc atgaaatgcc cactactatg ttttatgtat atctttgtag    900
attagcattt cctgtggagg aaaataacag aagcttgaag aaaatcccca cactcgaaga    960
tctagctaag tactcaatca ttggactaaa ggtataaaat agaaaaataa tattctttgt   1020
aggaatcaac attcctagag gactttataa tcatgtttct ttgcagccaa gacgagctga   1080
tctcgacatg aaccatcatg tcaataattt ccctatatt ggatggattc ttgaggttag   1140
tgtcatcatc aggttctttt taaaataata acttcagtaa tcaccatatg actttgtttt   1200
```

```
ctgatattgt cagagcatac tcaagagatt gtagacacgc atgaactttg gattacagac    1260
gagaatgtca gcaagacgat gtggtggatt cactcaccac ctcaaagaat ggctctgcaa    1320
catcaggcac acaaagccac aacgatagcc agttcttatc tggagatggt caggagatca    1380
actgtgggac aaccctgtgg agaaagaagc cctccagata dacaatccct aagccattac    1440
gagtcaagga ccaatcattt tcacataaac ctctttgctt atttgattaa acaagttaca    1500
tgactgataa cagattctgc ctattacaaa gtctcataaa tttcaaataa tgtgagtaaa    1560
taaatagaaa acagagaatt gg                                            1582

<210> SEQ ID NO 2
<211> LENGTH: 681
<212> TYPE: DNA
<213> ORGANISM: Brassica napus

<400> SEQUENCE: 2
ggataaatgt cttctccatc tcctgttccc atataagaaa acctggtttg agtcctctgc      60
gggcggctgt atctgctgat caagaaagtg tgattcgagc agaacaaggt ttggacacac     120
tcgcgggtcg gctccggttg ggtagcttga cggaggatgg tttatcgtat aaagagaagt     180
tcatagtcag atcccacgaa gtgcagagta acaaaaccgc tacggtccaa accattgcca     240
atcttttgca ggttagattg tagtttgttt aaaactatgt atgaatcttg attggtcaat     300 atttttaaaaa taagaatttt attttgttgg tttgatgtat ttaggaggtg ggatgtaatc     360
agtttcagag cgttggattt tcgactgatg ggtttgcgac aacacctacc atgaggaaac     420
tgaatctcat ttgggtcact tcgagaatgc acattggga ttacaaatat ccagcttggt     480
atttttttct tctgctgtgt atgttttgat gacacaacaa atgagcagag attttgaaat     540
ttttggttac aggggtgatg tggttgagat agagacatgg tgtcagagtg aaggaaggat     600
cgggacaagg catgattgga ttcttaagga tgttgctaac ggtgaagtca ctggccgtac     660
tactaggttt ccctctcatc a                                              681

<210> SEQ ID NO 3
<211> LENGTH: 664
<212> TYPE: DNA
<213> ORGANISM: Artificial Sequence
<220> FEATURE:
<223> OTHER INFORMATION: from Brassica napus

<400> SEQUENCE: 3
ggataaatgt cttctccatc tcctgttccc atataagaaa acctggtttg agtcctctgc      60
gggcggctgt atctgctgat caagaaagtg tgattcgagc agaacaaggt ttggacacac     120
tcgcgggtcg gctccggttg ggtagcttga cggaggatgg tttatcgtat aaagagaagt     180
tcatagtcag atcccacgaa gtgcagagta acaaaaccgc tacggtccaa accattgcca     240
atcttttgca ggttagattg tagtttgttt aaaactatgt atgaatcttg attggtcaat     300 atttttaaaaa taagaatttt attttgttgg tttgatgtat ttaggaggtg ggatgtaatc     360
agtttcagag cgttggattt tcgactgatg ggtttgcgac aacacctacc atgaggaaac     420
tgaatctcat ttgggtcact tcgagaatgc acattggga ttacaaatat ccagcttggt     480
atttttttct tctgctgtgt atgttttgat gacacaacaa atgagcagag attttgaaat     540
ttttggttac aggggtgatg tggtgtcaga gtgaaggaag gatcgggaca aggcatgatt     600
ggattcttaa ggatgttgct aacggtgaag tcactggccg tactactagg tttccctctc     660
atca                                                                 664
```

<210> SEQ ID NO 4
<211> LENGTH: 51
<212> TYPE: DNA
<213> ORGANISM: Brassica napus

<400> SEQUENCE: 4
aggggtgatg tggttgagat agagacatgg tgtcagagtg aaggaaggat c    51

<210> SEQ ID NO 5
<211> LENGTH: 16
<212> TYPE: PRT
<213> ORGANISM: Brassica napus

<400> SEQUENCE: 5

Gly Asp Val Val Glu Ile Glu Thr Trp Cys Gln Ser Glu Gly Arg Ile
1               5                   10                  15

<210> SEQ ID NO 6
<211> LENGTH: 34
<212> TYPE: DNA
<213> ORGANISM: Artificial Sequence
<220> FEATURE:
<223> OTHER INFORMATION: from Brassica napus

<400> SEQUENCE: 6
aggggtgatg tggtgtcaga gtgaaggaag gatc    34

<210> SEQ ID NO 7
<211> LENGTH: 671
<212> TYPE: DNA
<213> ORGANISM: Artificial Sequence
<220> FEATURE:
<223> OTHER INFORMATION: from Brassica napus

<400> SEQUENCE: 7
ggataaatgt cttctccatc tcctgttccc atataagaaa acctggtttg agtcctctgc    60
gggcggctgt atctgctgat caagaaagtg tgattcgagc agaacaaggt ttggacacac   120
tcgcgggtcg gctccggttg ggtagcttga cggaggatgg tttatcgtat aaagagaagt   180
tcatagtcag atcccacgaa gtgcagagta acaaaaccgc tacggtccaa accattgcca   240
atcttttgca ggttagattg tagtttgttt aaaactatgt atgaatcttg attggtcaat   300
attttaaaaa taagaatttt attttgttgg tttgatgtat ttaggaggtg ggatgtaatc   360
agtttcagag cgttggattt tcgactgatg ggtttgcgac aacacctacc atgaggaaac   420
tgaatctcat ttgggtcact tcgagaatgc acattgagat ttacaaatat ccagcttggt   480
attttttttt tgctgtgtat gttttgatga cacaacaaat gagcagagat tttgaaattt   540
tggtataggg gtgatgtggt tgagacatgg tgtcagagtg aaggaaggat cgggacaagg   600
cgtgattgga ttcttaagga tcttgctaac ggtgaagtca ctggccgtac tactaggttt   660
ccctctcatc a                                                         671

<210> SEQ ID NO 8
<211> LENGTH: 45
<212> TYPE: DNA
<213> ORGANISM: Artificial Sequence
<220> FEATURE:
<223> OTHER INFORMATION: from Brassica napus

<400> SEQUENCE: 8
aggggtgatg tggttgagac atggtgtcag agtgaaggaa ggatc    45

<210> SEQ ID NO 9
<211> LENGTH: 489
<212> TYPE: DNA
<213> ORGANISM: Brassica napus

<400> SEQUENCE: 9

```
tcaatcttga ttggtggaat ttgtaaagac aagaactttg ttggttggtt gatgtgtata      60
ttataggagg tgggatgtaa tcatgcgcag agcgttggat ctcgactga tgggtttgcg      120
acaacaccga caatgaggaa actgcatctc atttgggtca ctgcgagaat gcatatagag     180
atctacaagt accctgcttg gtatttggtt tctgcttcgt ttcttttat ctatgtgtct      240
ctgttttgat gacaacttaa tgagaggaat cttttggtta caggggtgat gtggttgaga     300
tagagacatg gtgtcagagt gaaggaagga tcgggactag gcgtgattgg attcttaagg    360
atgttgctac gggtgaagtc actggccgtg ctacaaggtt tccttttcat cattttttt     420
tagcttcctg gattggtttg gacctttatg ttccgtattt aatggtattg tcgtgatttg    480
ttgttttgac                                                             489
```

<210> SEQ ID NO 10
<211> LENGTH: 483
<212> TYPE: DNA
<213> ORGANISM: Artificial Sequence
<220> FEATURE:
<223> OTHER INFORMATION: from Brassica napus

<400> SEQUENCE: 10

```
tcaatcttga ttggtggaat ttgtaaagac aagaactttg ttggttggtt gatgtgtata      60
ttataggagg tgggatgtaa tcatgcgcag agcgttggat ctcgactga tgggtttgcg      120
acaacaccga caatgaggaa actgcatctc atttgggtca ctgcgagaat gcatatagag     180
atctacaagt accctgcttg gtatttggtt tctgcttcgt ttcttttat ctatgtgtct      240
ctgttttgat gacaacttaa tgagaggaat cttttggtta caggggtgat gtggttgaga     300
catggtgtca gagtgaagga aggatcggga ctaggcgtga ttggattctt aaggatgttg    360
ctacgggtga agtcactggc cgtgctacaa ggtttccttt tcatcatttt ttttagctt     420
cctggattgg tttggacctt tatgttccgt atttaatggt attgtcgtga tttgttgttt    480
gac                                                                    483
```

<210> SEQ ID NO 11
<211> LENGTH: 56
<212> TYPE: DNA
<213> ORGANISM: Brassica napus

<400> SEQUENCE: 11

```
gttacagggg tgatgtggtt gagatagaga catggtgtca gagtgaagga aggatc         56
```

<210> SEQ ID NO 12
<211> LENGTH: 50
<212> TYPE: DNA
<213> ORGANISM: Artificial Sequence
<220> FEATURE:
<223> OTHER INFORMATION: from Brassica napus

<400> SEQUENCE: 12

```
gttacagggg tgatgtggtt gagacatggt gtcagagtga aggaaggatc               50
```

<210> SEQ ID NO 13

```
<211> LENGTH: 507
<212> TYPE: DNA
<213> ORGANISM: Brassica napus

<400> SEQUENCE: 13
gattttcgac tgatgggttt gcaacaacac ctaccatgag gaaactgaat ctcatttggg      60
tcacttcgag aatgcacatt gagatttaca aatatccagc ttggtatttt ttttttgctg     120
tgtatgtttt gatgacacaa caaatgagca gagattttga aattttggta tagggggtgat    180 gtggttgaga tagagacatg gtgtcagagt gaaggaagga tcgggacaag gcgtgattgg     240
attcttaagg atcttgctaa cggtgaagtc actggccgtg ctactaggtt tccctctcat     300
cattgttagc tttctccatt ggtttgtgca atggaattaa attttcttat gttaaagata     360
taattttcag ttacttggat ttatgggact gtcatgattt gttgtaccta tgtttgtgtt     420
actgtttcag caagtgggtg atgatgaacc aagacacaag acggctacag aaagtttctg     480
atgatatccg ggacgagcac ttgattt                                         507

<210> SEQ ID NO 14
<211> LENGTH: 483
<212> TYPE: DNA
<213> ORGANISM: Artificial Sequence
<220> FEATURE:
<223> OTHER INFORMATION: from Brassica napus

<400> SEQUENCE: 14
gattttcgac tgatgggttt gcaacaacac ctaccatgag gaaactgaat ctcatttggg      60
tcacttcgag aatgcacatt gagatttaca aatatccagc ttggtatttt ttttttgctg     120
tgtatgtttt gatgacacaa caaatgagca gagattttga aattttggta tagggggtgat    180 gtggttgaag gaaggatcgg gacaaggcgt gattggattc ttaaggatct tgctaacggt     240
gaagtcactg gccgtgctac taggtttccc tctcatcatt gttagctttc tccattggtt     300
tgtgcaatgg aattaaattt tcttatgtta aagatataat tttcagttac ttggatttat     360
gggactgtca tgatttgttg tacctatgtt tgtgttactg tttcagcaag tgggtgatga     420
tgaaccaaga cacaagacgg ctacagaaag tttctgatga tatccgggac gagcacttga     480
ttt                                                                   483

<210> SEQ ID NO 15
<211> LENGTH: 69
<212> TYPE: DNA
<213> ORGANISM: Brassica napus

<400> SEQUENCE: 15 tatagggtg atgtggttga gatagagaca tggtgtcaga gtgaaggaag gatcgggaca      60
aggcgtgat                                                             69

<210> SEQ ID NO 16
<211> LENGTH: 21
<212> TYPE: PRT
<213> ORGANISM: Brassica napus

<400> SEQUENCE: 16

Gly Asp Val Val Glu Ile Glu Thr Trp Cys Gln Ser Glu Gly Arg Ile
  1               5                  10                  15

Gly Thr Arg Arg Asp
             20
```

```
<210> SEQ ID NO 17
<211> LENGTH: 45
<212> TYPE: DNA
<213> ORGANISM: Artificial Sequence
<220> FEATURE:
<223> OTHER INFORMATION: from Brassica napus

<400> SEQUENCE: 17 tatagggtg atgtggttga aggaaggatc gggacaaggc gtgat           45

<210> SEQ ID NO 18
<211> LENGTH: 517
<212> TYPE: DNA
<213> ORGANISM: Brassica napus

<400> SEQUENCE: 18
tatgaatgga aaaagtatc aatctttgta attatgaatc ttgattggtc aattgtgaaa    60
gacaagaact tgttggttg attgatgtgt ataggagg tgggatgtaa tcatgctcag     120
agcgtaggat tctcgactga tgggtttgcg acaacaccta ccatgaggaa attgcatctc   180
atttgggtca ctgccagaat gcacattgag atctacaagt accctgcttg gtattggttt   240
ctgcttcatc tgtctatcta tctagatgtg tctctgtttt gatgacaact aacgaggaat   300
ctttcggttt acaggggtga tgtggttgag atagagacat ggtgtcagag tgaaggaagg   360
atcgggacta ggcgtgattg gattcttaag gatgttgcta ccggtgaagt cactggccgt   420
gctacaaggt ttccttttca tcattttttt agcttccggg attggtttgg gaccttaatg   480
ttccgtattt tatggtgctg tcctgatttg ttgtttg                            517

<210> SEQ ID NO 19
<211> LENGTH: 493
<212> TYPE: DNA
<213> ORGANISM: Artificial Sequence
<220> FEATURE:
<223> OTHER INFORMATION: from Brassica napus

<400> SEQUENCE: 19
tatgaatgga aaaagtatc aatctttgta attatgaatc ttgattggtc aattgtgaaa    60
gacaagaact tgttggttg attgatgtgt ataggagg tgggatgtaa tcatgctcag     120
agcgtaggat tctcgactga tgggtttgcg acaacaccta ccatgaggaa attgcatctc   180
atttgggtca ctgccagaat gcacattgag atctacaagt accctgcttg gtattggttt   240
ctgcttcatc tgtctatcta tctagatgtg tctctgtttt gatgacaact aacgaggaat   300
ctttcggttt acaggggtga tgtggttgaa ggaaggatca ggactaggcg tgattggatt   360
cttaaggatg ttgctaccgg tgaagtcact ggccgtgcta caaggtttcc ttttcatcat   420 tttttagct tccgggattg gtttgggacc ttaatgttcc gtattttatg gtgctgtcct    480
gatttgttgt ttg                                                      493

<210> SEQ ID NO 20
<211> LENGTH: 74
<212> TYPE: DNA
<213> ORGANISM: Brassica napus

<400> SEQUENCE: 20
cggtttacag gggtgatgtg gttgagatag agacatggtg tcagagtgaa ggaaggatcg    60
ggactaggcg tgat                                                      74

<210> SEQ ID NO 21
```

```
<211> LENGTH: 50
<212> TYPE: DNA
<213> ORGANISM: Artificial Sequence
<220> FEATURE:
<223> OTHER INFORMATION: from Brassica napus

<400> SEQUENCE: 21
cggtttacag gggtgatgtg gttgaaggaa ggatcaggac taggcgtgat         50
```

ENGINEERED NUCLEASES TO GENERATE DELETION MUTANTS IN PLANTS

CROSS-REFERENCE TO RELATED APPLICATIONS

This application is a national phase application of international application PCT/US2017/034541, filed May 25, 2017, entitled ENGINEERED NUCLEASES TO GENERATE DELETION MUTANTS IN PLANTS, which application claims the benefit of U.S. Provisional Patent Application Ser. No. 62/341,489, filed on May 25, 2016, entitled ENGINEERED NUCLEASES TO GENERATE DELETION MUTANTS IN PLANTS, which application is hereby incorporated by reference herein in its entirety.

BACKGROUND OF THE INVENTION

In recent years, diets high in saturated fats have been associated with increased levels of cholesterol and increased risk of coronary heart disease. As such, current dietary guidelines indicate that saturated fat intake should be no more than 10 percent of total calories. Based on a 2,000-calorie-a-day diet, this is about 20 grams of saturated fat a day. Oils contain saturated fats. For example canola oil typically contains about 7% to 8% saturated fatty acids. A decrease in saturated fatty acid content would improve the nutritional profile of oils.

SUMMARY OF THE INVENTION

Genes involved in plant oil synthesis, including those that regulate saturated fatty acid and oleic acid content, have been mutated by a process which involves exposing seeds to chemicals or radiation in order to generate mutants with desirable traits. Unlike plants modified with engineered nucleases, in which a mutation (substitution, deletion and/or addition of one or more nucleotides) can be engineered to occur at a very specific location in the plant genome, plants developed via mutagenic processes often result in random, multiple and unspecific genetic changes. These random, multiple genetic changes all come together to provide the phenotype of the mutated plant. With engineered nucleases, a very specific mutation, or set of mutations, can be generated and their effect on phenotype (e.g., oil profile) can be determined.

Provided herein is the production of mutant FatA1, FatA2, Kas2, Kas3 and/or FatB, allele(s) generated by the use of engineered nucleases, plants comprising said one or more mutant alleles of FatA1, FatA2, Kas2, Kas3 and/or FatB, such as *Brassica* plants, and uses of such plants produce lower saturated fatty acid content. As described herein, *Brassica* plants containing such mutations can produce oils with reduced saturated fatty acid content. *Brassica* plants described herein are particularly useful for producing canola oils for certain food applications, as the plants are not genetically modified.

Provided herein are *Brassica* plants (e.g., *Brassica napus, Brassica juncea*, or *Brassica rapa* plants) and progeny thereof (e.g., seeds) that include substitution, deletion and/or insertion mutations in one or more alleles of FatA1, FatA2, Kas2, Kas3 and/or FatB via engineered nucleases, wherein each mutated allele results in the production of a FatA1, FatA2, Kas2, Kas3 and/or FatB polypeptide having reduced or no activity relative to a corresponding wild-type FatA1, FatA2, Kas2, Kas3 and/or FatB polypeptide (alternatively the substitution, deletion and/or insertion may result in no FatA1, FatA2, Kas2, Kas3 and/or FatB protein/activity being produced). A mutated allele can include a nucleic acid encoding a truncated FatA1, FatA2, Kas2, Kas3 and/or FatB polypeptide. A mutated allele can include a sequence having at least 75%, 80%, 85%, 90%, 95%, 96%, 97%, 98%, or 99% sequence identity to the nucleotide sequence of the wild-type allele (e.g., SEQ ID NO: 1 for FatA1).

One embodiment provides a method to produce a plant with reduced saturated fatty acids comprising: a) contacting a plant with an engineered nuclease specific for FatA1, FatA2, Kas2, Kas3 and/or FatB gene(s); b) growing the plant from step a) and collecting the seeds from said plant; and c) selecting plants grown from the seeds of step b) with a substitution, deletion and/or insertion mutation in one or more of said genes; wherein said substitution, deletion and/or insertion mutation results in a reduced production of saturated fatty acids by said plant as compared to a control plant of identical genetic background that has not been mutated by said gene editing.

Another embodiment provides a method to produce a plant with reduced saturated fatty acids comprising: a) contacting a plant cell or tissue with an engineered nuclease specific for FatA1, FatA2, Kas2, Kas3 and/or FatB gene(s); b) generating a plant from the plant cell or tissue in step a); c) selecting plants of step b) with a substitution, deletion and/or insertion mutation in one or more of said genes; wherein said substitution, deletion and/or insertion mutation results in a reduced production of saturated fatty acids by said plant as compared to a control plant of identical genetic background that has not been mutated by said gene editing.

In one embodiment, the plant is a *Cruciferae* plant. In another embodiment, the plant is a *Brassica* plant. In another embodiment, the plant is *Brassica napus, Brassica juncea*, or *Brassica rapa*.

In one embodiment, the engineered nuclease is a meganuclease. In one embodiment, there is a substitution, deletion and/or insertion mutation in at least one allele of FatA1. In another embodiment, there is a substitution, deletion and/or insertion mutation in at least one allele of FatA2. In another embodiment, there is a substitution, deletion and/or insertion mutation in at least one allele of Kas2. In one embodiment, there is a substitution, deletion and/or insertion mutation in at least one allele of Kas3. In another embodiment, there is a substitution, deletion and/or insertion mutation in at least one allele of FatB.

One embodiment provides a *Brassica* plant comprising a deletion in at least one allele of FatA1, FatA2, Kas2, Kas3 and/or FatB, In one embodiment, the deletion is from about 1 to about 350 base pairs in length. In another embodiment, the deletion results in a decrease in saturated fatty acid.

In one embodiment, the recognition/target sequence comprises any contiguous nucleotide (e.g., 10 or more) sequence of the FatA1 gene (SEQ ID NO: 1).

In another embodiment, provided herein is a method of producing an oil. The method includes crushing seeds produced from at least one plant described herein and extracting the oil from the crushed seeds.

One embodiment provides a method to mutate the genome of a *Brassica* plant cell at a target sited comprising: a) inducing a double stranded DNA break at a target site, said double stranded break being induced by the introduction to said cell of a double stranded DNA break inducing (DSBI) enzyme which recognizes a recognition sequence in the vicinity of or at said target site in FatA1, FatA2, Kas2, Kas3 and/or FatB gene(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof. In one embodiment, the plant cell is regenerated into a plant. One embodiment provides a plant cell comprising a mutation at a target site of the genome obtained by the methods provided herein. Another embodiment provides a plant, plant part, seed or propagating material thereof comprising a mutation at a target site of the genome comprising the plant cell.

One embodiment provides a method to produce a *Brassica* plant with reduced saturated fatty acids comprising: a) inducing a double stranded DNA break at a target site, said double stranded break being induced by the introduction to a plant cell of a double stranded DNA break inducing (DSBI) enzyme which recognizes a recognition sequence in the vicinity of or at said target site in FatA1, FatA2, Kas2, Kas3 and/or FatB gene(s); and b) selecting a plant cell wherein said double stranded DNA break has been repaired resulting in a mutation in the genome at said target site, wherein said mutation is a substitution of at least one nucleotide, a deletion of at least one nucleotide, an insertion of at least one nucleotide or any combination thereof; and c) regenerating said plant cell(s) of b) into a plant; wherein said mutation results in reduced production of saturated fatty acids by said plant as compared to a control plant of identical genetic background that has not been mutated by said DSBI and repair.

In one embodiment, the DSBI enzyme is a single chain meganuclease or a pair of meganucleases which recognizes or recognize in concert a site and induces or induce said double strand break.

In one embodiment, the plant(s) produced by the methods described herein is crossed with another plant.

One embodiment provides a plant, plant part, seed or propagating material thereof comprising a modification at a target site of the genome obtained by the methods provided here.

In one embodiment, the plant is *Brassica napus. Brassica juncea*, or *Brassica rapa*.

In one embodiment, one or both FatA1 alleles on N3, N7, 13 and/or N17 are mutated. In another embodiment, one or both FatA1 alleles on N13 and/or N17 are mutated. In one embodiment, one or both FatA1 alleles on N13 are mutated. In another embodiment, one or both FatA1 alleles on N3, N7 and/or N13 are mutated. In one embodiment, one or both FatA1 alleles on N7 are mutated. In one embodiment, the mutation is a deletion of one or more nucleotides, optionally comprising the substitution of at least one nucleotide.

In one embodiment, the plants produced by the methods described herein yield a reduction of stearic acid (18:0) of about 9% to about 35% as compared to a non-mutated plant of identical genetic background. In another embodiment, the plants yield an overall reduction in total saturated fatty acids of about 5 to about 15%.

BRIEF DESCRIPTION OF THE DRAWINGS

FIG. 1 provides full-length wild-type sequence for FatA1 from the public *Brassica napus* sequence (Chalhoub, et al., 2014): BnaA03g47660D. (SEQ ID NO:1) An NCBI accession number for a FatA1 mRNA sequence is XM_013833775.1.

FIGS. 2A-E provide A) a partial wild-type sequence for FatA1 (N13; SEQ ID NO:2); B) depicts partial sequence for a FatA1 N13 mutant in a IMC201 background (17 bp deletion in N13; SEQ ID NO:3); C) depicts the meganuclease recognition site, partial wild type FatA1 nucleotide sequence (SEQ ID NO:4), partial wild-type protein sequence (SEQ ID NO:5) and partial mutant sequence depicting deletion (SEQ ID NO:6); D) depicts partial sequence for a FatA1 N13 mutant in a Cargill background represented by American Type Culture Collection (ATCC) Accession No. PTA-12314, PTA-12315 and PTA-12316 (6 bp deletion in N13; SEQ ID NO:7); and E) depicts the meganuclease recognition site, partial wild type FatA nucleotide sequence (SEQ ID NO:4), partial protein sequence (SEQ ID NO:5) and mutant sequence depicting deletion (SEQ ID NO:8).

FIGS. 3A-C provide A) a partial wild-type sequence for FatA1 (N7; SEQ ID NO:9); B) depicts partial sequence for a FatA1 N7 mutant in a IMC201 background (6 bp deletion in N7; SEQ ID NO:10); and C) depicts the meganuclease recognition site, partial wild type FatA1 nucleotide sequence (SEQ ID NO:11), partial wild-type protein sequence (SEQ ID NO:5) and partial mutant sequence depicting deletion (SEQ ID NO:12).

FIGS. 4A-C provide A) a partial wild-type sequence for FatA1 (N3; SEQ ID NO:13); B) depicts partial sequence for a FatA1 N3 mutant in a IMC201 background (24 bp deletion in N3; SEQ ID NO:14); and C) depicts the meganuclease recognition site, partial wild type FatA1 nucleotide sequence (SEQ ID NO:15), partial wild-type protein sequence (SEQ ID NO:16) and partial mutant sequence depicting deletion (SEQ ID NO:17).

FIGS. 5A-C provide A) a partial wild-type sequence for FatA1 (N17, SEQ ID NO:18); B) depicts partial sequence for a FatA1 N17 mutant in a Cargill background represented by American Type Culture Collection (ATCC) Accession No. PTA-12314, PTA-12315 and PTA-12316 (24 bp deletion and 1 bp change (bold and underlined A) in N17; SEQ ID NO:19); and C) depicts the meganuclease recognition site, partial wild type FatA1 nucleotide sequence (SEQ ID NO:20), partial wild-type protein sequence (SEQ ID NO:16) and partial mutant sequence depicting deletion and 1 bp change (highlighted in blue) (SEQ

DETAILED DESCRIPTION OF THE INVENTION

Figure 4C:
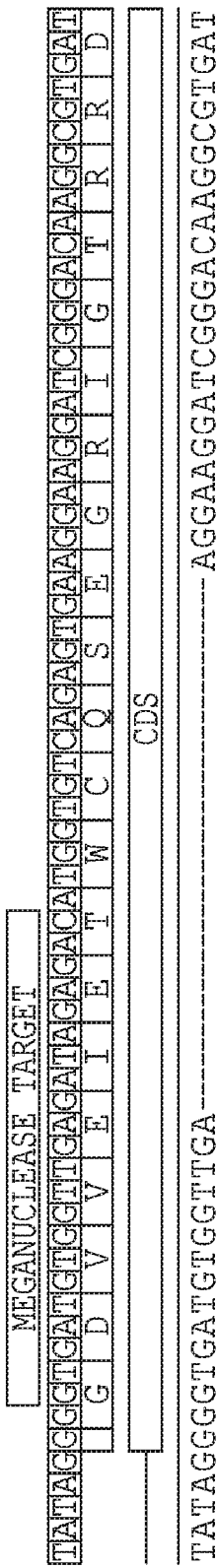

Methods are provided to mutate, in a targeted manner, the genome of a plant using a double stranded DNA break inducing enzyme. Also provided are plants, in particular *Brassica* plants, which yield seeds producing oils having a reduced saturated fatty acid content; and method for making such plants.

The invention provides methods to introduce a targeted mutation, including insertion, deletion, or substitution of one or more nucleotides, at a precisely localized nucleotide sequence in the genome of a plant using engineered double stranded DNA break inducing enzymes. The invention further provides a plant cell, plant part, plant or seed comprising such a mutated sequence, wherein said mutation results in a reduction of saturated fatty acid production by the plant, and methods for making such plant.

The invention is based on the observation that functional meganucleases can be engineered to specifically recognize and cleave a nucleotide sequence, such as FatA1 (SEQ ID NO: 1), in a plant cell, from which a plant can be produced. Provided herein are plants made by the methods provided herein, such as *Brassica* plants including *B. napus, B. juncea*, and *B. rapa* species of *Brassica*, that yield seeds producing oils having a reduced saturated fatty acid content.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, a "double stranded DNA break endonuclease" is an enzyme capable of inducing a double stranded DNA break at a particular nucleotide sequence, called the "recognition site." Homing endonucleases constitute a family of endonucleases and are sometimes also referred to as meganucleases. They may be encoded by introns, independent genes or intervening sequences, and present structural and functional properties that distinguish them from the more classical restriction enzymes, usually from bacterial restriction-modification Type II systems.

A person skilled in the art would be able to either choose a double stranded DNA break inducing ("DSBI") enzyme recognizing the selected target nucleotide sequence to engineer such a DSBI endonuclease.

As used herein "located in the vicinity" refers to the site of double DNA stranded break induction, i.e. the recognition site of the DSBI enzyme, being located at a distance of 10 bp, 20 bp, 30 bp, 50 bp, 60 bp, 70 bp, 80 bp, 90 bp, 100 bp, 200, 250 bp, 500 bp, 1 kbp, 2 kbp, 3 kbp, 4 kbp, 5 kbp to 10 kbp from the target, i.e. the site in the genomic DNA which is to be mutated (the target site).

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism).

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). The term knockout, inactivated, and disrupted are used interchangeably herein to mean that the targeted site is changed so that the gene expression product is eliminated or greatly reduced or the product expressed has reduced activity as compared to a control (e.g., wild type protein). Also known as knockout organisms or simply knockouts. The term also refers to the process of creating such an organism, as in "knocking out" a gene.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage; refers to the number of positions in the two optimally aligned sequences which have identical residues ($\times 100$) divided by the number of positions compared. A gap, i.e. a position in an alignment where a residue is present in one sequence but not in the other, is regarded as a position with non-identical residues. The optimal alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleic acids can be DNA or RNA, single- or double-stranded. Nucleic acids can be synthesized chemically or produced by biological expression in vitro or in vivo. Nucleic acids can be chemically synthesized using appropriately protected ribonucleoside phosphoramidites and a conventional DNA/RNA synthesizer. DNA includes cDNA and genomic DNA.

Standard recombinant DNA and molecular cloning techniques used herein are well known in the art and are described more fully in Sambrook; J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

The terms "comprises," "comprising," and the like can have the meaning ascribed to them in U.S. Patent Law and can mean "includes," "including" and the like. As used herein, "including" or "includes" or the like means including, without limitation.

Brassica Plants

Brassica plants described herein have reduced levels of total saturated fatty acids in the seed oil as a result of reduced activity of FatA1, FatA2, Kas2, Kas3 and/or FatB. It is understood that throughout the disclosure, reference to "plant" or "plants" includes progeny, i.e., descendants of a particular plant or plant line, as well as cells or tissues from the plant. Progeny of an instant plant include seeds formed on $F_1$, $F_2$, $F_3$, $F_4$ and subsequent generation plants, or seeds formed on $BC_i$, $BC_2$, $BC_3$, and subsequent generation plants. Seeds produced by a plant can be grown and then selfed (or outcrossed and selfed, or doubled through dihaploid) to obtain seeds homozygous for a mutant allele. The term "allele" or "alleles" refers to one or more alternative forms of a gene at a particular locus.

Reduced activity, including absence of detectable activity, of FatA1, FatA2, Kas2, Kas3 and/or FatB, can be achieved by mutating one or more endogenous FatA1, FatA2, Kas2, Kas3 and/or FatB allele(s) (each of these genes has one or more isoforms, for example, FatA1 has 4 isoforms, namely one on each of chromosome N3, N13, N7 and N17). An endogenous isoform/allele of FatA1, FatA2, Kas2, Kas3 and/or FatB allele can be mutated (deletion, addition and/or substitution mutation) by the use of engineered nucleases.

Genetic mutations can be introduced within, for example, regenerable plant tissue using one or more engineered nucleases. The treated population, or a subsequent generation of that population, can be screened for reduced protein activity that results from the mutation, e.g., by determining the fatty acid profile of the population and comparing it to a corresponding non-mutagenized population. Mutations can be in any portion of a gene, including coding sequence, intron sequence and regulatory elements, that render the resulting gene product non-functional or with reduced activity.

The plants on which the genetic mutations can be carried out are any plants, including those in the *Brassica* family, including any wild-type and mutant plant backgrounds. Such *Brassica* plants include, but are not limited to, IMC201 (U.S. Pat. No. 9,334,483), IMC02 (represented by American Type Culture Collection (ATCC) Accession No. PTA-6221), Westar (U.S. Pat. No. 6,342,658), 1904 (represented by American Type Culture Collection (ATCC) Accession No. PTA-11273, as well as progeny of the seed designated 1904 and represented by ATCC Accession No, PTA-11273), 2558 (represented by American Type Culture Collection (ATCC) Accession No. PTA-11274, as well as progeny of the seed designated 2558 and represented by ATCC Accession No. PTA-11274), US Pub Appln No. 2013/0081156, 95CB504 (U.S. Pat. No. 9,334,483), Cargill background (represented by American Type Culture Collection (ATCC) Accession No. PTA-12314, PTA-12315 and PTA-12316), 03LC LL and hybrid backgrounds deposited as Accession No. PTA-12314, PTA-12315 and PTA-12316, and Topas (represented by American Type Culture Collection (ATCC) Accession No. PTA-120738).

Engineered Nucleases

The use of engineered nucleases (GEEN) is a type of genetic engineering in which DNA is inserted, deleted or substituted in the genome of an organism using engineered nucleases, or "molecular scissors." These nucleases create site-specific double-strand breaks (DSBs) at desired locations in the genome. The induced double-strand breaks are repaired resulting in targeted mutations, such as deletions.

There are currently four families of engineered nucleases being used: meganucleases, zinc finger nucleases (ZFNs), Transcription Activator-Like Effector-based Nucleases (TALEN), and the CRISPR-Cas system (Esvelt, K M. and Wang, H H. (2013). "Genome-scale engineering for systems and synthetic biology." Mol Syst Biol 9 (1): 641; Tan, W S. et al. (2012). "Precision editing of large animal genomes." Adv Genet 80: 37-97; Puchta, H. and Fauser, F. (2013). "Gene targeting in plants: 25 years later." Int. J. Dev. Biol 57: 629-637; Boglioli., E. and Richard, M. "Rewriting the book of life: a new era in precision genome editing" (PDF). Boston Consulting Group; Method of the Year 2011. Nat Meth 9 (1), 1-1; www.sciencemag.org/topic/2015-breakthrough-year).

Meganucleases, found commonly in microbial species, have the unique property of having long recognition sequences (>14 bp) thus making them naturally specific (de Souza, N., Primer: genome editing with engineered nucleases. Nat Meth 9 (1), 27-27 (2011); Smith, J. et al., A combinatorial approach to create artificial homing endonucleases cleaving chosen sequences. Nucleic Acids Research 34 (22), e149 (2006)). This can be exploited to make site-specific DSB in genome editing. Meganuclease variants that recognize unique sequences have been created (Id). Also of use is the fusion of various meganucleases to create hybrid enzymes that recognize a new sequence (Chevalier, B. S. et al., Design, Activity, and Structure of a Highly Specific Artificial Endonuclease" Molecular Cell 10 (4), 895-905 (2002)). Yet others have altered the DNA interacting amino acids of the meganuclease to design sequence specific meganucelases in a method named rationally designed meganuclease (U.S. Pat. No. 8,021,867; WO2007/047859; WO2011/064736).

A well characterized megaendonuclease is I-SceI. I-SceI is a site-specific endonuclease, responsible for intron mobility in mitochondria in *Saccharomyces cerevisea*. The enzyme is encoded by the optional intron Sc LSU.1 of the 21 S rRNA gene and initiates a double stranded DNA break at the intron insertion site generating a 4 bp staggered cut with 3'0H overhangs. The recognition site of I-SceI endonuclease extends over an 18 bp non-symmetrical sequence (Colleaux et al, 1988 Proc. Natl. Acad. Sci. USA 85: 6022-6026). The amino acid sequence for I-SceI and a universal code equivalent of the mitochondrial I-SceI gene have been provided by e.g. WO96/14408. WO 96/14408 further discloses a number of variants of I-SceI protein which are still functional. PCT application PCT/EP04/013122 (incorporated herein by reference) provides synthetic nucleotide sequence variants of I-SceI which have been optimized for expression in plants.

Another well characterized designed meganuclease is based on the naturally occurring meganuclease I-CreI for use as a scaffold. I-CreI is an endonuclease found in the chloroplasts of *Chlamydomonas rheinhardti* (Thompson et al. 1992, Gene 119, 247-251). This endonuclease is a homodimer that recognizes a pseudo-palindromic 22 bp DNA site in the 23SrRNA gene and creates a double stranded DNA break that can be used for the introduction of an intron. I-CreI is a member of a group of endonucleases carrying a single LAGLIDADG (SEQ ID NO: motif, LAGLIDADG (SEQ ID NO: 22) enzymes contain one or two copies of the consensus motif. Single-motif enzymes, such as I-CreI function as homodimers, whereas double-motif enzymes are monomers with two separate domains. Accordingly, when designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease, or may also be achieved by promoting the formation of heterodimers, as described e.g. in WO2007/047859.

A list of other DSB inducing enzymes and their respective recognition sites is provided in Table I of WO 03/004659 (pages 17 to 20) (incorporated herein by reference). These include I-See I, I-Chu I, I-Dmo I, I-Cre I, I-Csm I, PI-Fli I, Pt-Mtu I, I-Ceu I, I-See H, I-See III, HO, PI-Civ I, PI-Ctr I, PI-Aae I, PI-BSU I, PI-DhaI, PI-Dra I, PI-May I, PI-Mch PI-Mfu I, PI-Mfl I, PI-Mga I, PI-Mgo I, PI-Min I, PI-Mka I, PI-Mle I, PI-Mma I, PI-Msh PI-Msm I, PI-Mth I, PI-Mtu I, PI-Mxe I, PI-Npu I, PI-Pfu I, PI-Rma I, PI-Spb I, PI-Ssp I; PI-Fae I, PI-Mja I, PI-Pho I, PI-Tag I, PI-Thy I, PI-Tko I or PI-Tsp I.

As opposed to meganucleases, the concept behind ZFNs and TALEN technology is based on a non-specific DNA cutting enzyme, which can then be linked to specific DNA sequence recognizing peptides, such as zinc fingers (such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530)) and transcription activator-like effectors (TALEs; Baker, M., Gene-editing nucleases. Nat Meth 9 (1), 23-26 (2012); Christian et al., 2010, Genetics 186: 757-761, WO10/079430 and WO10/146121). In these technologies, the endonuclease has a DNA recognition site and cleaving site separate from each other. Although the nuclease portions of both ZFNs and TAI EN constructs have similar properties (e.g., FokI), the difference between these engineered nucleases is in their DNA recognition peptide. ZFNs rely on Cys2-His2 zinc fingers and TALEN constructs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities (de Souza, N., Primer: genome editing with engineered nucleases. Nat Meth 9 (1), 27-27 (2011)). Zinc fingers have been more established in these terms and approaches such as modular assembly (where Zinc fingers correlated with a triplet sequence are attached in a row to cover the required sequence); OPEN (low-stringency selection of peptide domains vs. triplet nucleotides followed by high-stringency selections of peptide combination vs. the final target in bacterial systems), and bacterial one-hybrid screening of zinc finger libraries among other methods have been used to make site specific nucleases.

Another way of producing custom-made meganucleases, by selection from a library of variants, is described in WO2004/067736. Custom made meganucleases with altered sequence specificity and DNA-binding affinity may also be obtained through rational design as described in WO2007/047859. Such custom designed endonucleases are also referred to as a non-naturally occurring endonucleases.

The designed double stranded break inducing enzyme may comprise, but need not comprise, a nuclear localization signal (NLS), such as the NLS of SV40 large T-antigen (Raikhel, Plant Physiol. 100: 1627-1632 (1992) and references therein) (Kalderon et al. Cell 39: 499-509 (1984)). The nuclear localization signal may be located anywhere in the protein, but is conveniently located at the N-terminal end of the protein. The nuclear localization signal may replace one or more of the amino acids of the double stranded break inducing enzyme.

Conveniently; the DSBI enzyme can be provided by expression of a plant expressible recombinant gene(s) encoding such enzyme(s). To this end, a DNA region comprising a nucleotide sequence encoding; for example, a designed meganuclease or meganuclease monomeric unit can be operably linked to a plant-expressible promoter and optionally a DNA region involved in transcription termination and polyadenylation and introduced into a plant, plant part or plant cell(s). The recombinant gene(s) encoding DSBI enzyme may be introduced transiently or stably. The DSBI enzyme may also be introduced into the plant, plant part or plant cell(s) by introducing into the cell an RNA molecule which is translated into the DSBI enzyme. Alternatively, the DSBI enzyme may be introduced into the plant, plant part or plant cell(s) directly as a protein. Methods for the introduction of DNA or RNA molecules or proteins into a plant, plant part, tissue or plant cell(s) are available to an art worker and briefly described below.

Described herein, the term "plant operative promoter" and "plant-expressible promoter" mean a promoter which is capable of driving transcription in a plant, plant tissue, plant organ, plant part, or plant cell. This includes any promoter of plant origin, but also any promoter of non-plant origin which is capable of directing transcription in a plant cell.

Promoters that may be used in this respect are constitutive promoters, such as the promoter of the cauliflower mosaic virus (CaMV) 35S transcript (Hapster et al., 1988, Md. Gen. Genet. 212: 182-190), the CaMV 19S promoter (U.S. Pat. No. 5,352,605; WO 84/02913; Benfey et al., 1989, EMBO J. 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, Plant Mal, Biol, 29:637-649), 'I'-DNA gene promoters such as the octopine synthase (OCS) and nopaline synthase (NOS) promoters from *Agrobacterium*, and further promoters of genes whose constitutive expression in plants is available to the person skilled in the art.

Further promoters that may be used in this respect are tissue-specific or organ-specific promoters, such as seed-specific promoters, such as the 2S albumin promoter (Josefson et al., 1987, J. Biol. Chem. 262:12196-12201), the phaseolin promoter (U.S. Pat. No. 5,504,200; Bustos et al., 1989, Plant Cell 1. (9):839-53), the legumine promoter (Shirsat et al., 1989, Mal. Gen. Genet. 215(2):326-331), the "unknown seed protein" (USP) promoter (Baumlein et al., 1991, Mal. Gen. Genet. 225(3):459-67), the napin promoter (U.S. Pat. No. 5,608,152; Stalberg et al., 1996, Planta 199: 515-519), the *Arabidopsis* oleosin promoter (WO 98/45461), the *Brassica* Bce4 promoter (WO 91/13980), and further promoters of genes whose seed-specific expression in plants is available to the person skilled in the art.

Plant Gene Editing

The use of meganucleases, ZFNs, CRISPR and TALEN, provides a novel strategy for genetic manipulation in plants and can assist in the engineering of desired plant traits by mutating endogenous genes.

Using engineered nucleases, or any method available to an art worker, various genes can be mutated (so as to create a deletion mutation/truncation, addition of one more nucleotides and/or mutating one or more nucleotides (changing its sequence/substitution) and not a mutation by insertion of foreign/non-endogenous DNA), including FatA1 (fatty acyl thioesterase A 1; Moreno-Perez et al, 2012. Reduced expression of FatA thioesterases in *Arabidopsis* affects the oil content and fatty acid composition of the seeds. Planta 235: 629-39; Hawkins & Kridl. 1998. Characterization of acyl-ACP thioesterases of mangosteen (*Garcinia mangostana*)

seed and high levels of stearate production in transgenic canola. Plant J 13: 743-52); FatA2 (fatty acyl thioesterase A 2; U.S. Pat. No. 9,334,483); Kas3 (Dehesh et al. 2001. Overexpression of 3-ketoacyl-acyl-carrier protein synthase Ills in plants reduces the rate of lipid synthesis. Plant Phys 125:1103-1114; Abbadi et al. 2000. Knockout of the regulatory site of 3-ketoacyl-ACP synthase III enhances short- and medium-chain acyl-ACP synthesis. Plant J 24: 1-9); Kas2 (Pidkowich et al. 2007. Modulating seed ii-ketoacyl-acyl carrier protein synthase II level converts the composition of a temperate seed oil to that of a palm-like tropical oil, PNAS 104:4742-4747; Wu et al. 1994, A mutant of *Arabidopsis* deficient in the elongation of palmitic acid. Plant Phys 106: 143-150; Gupta et al. 2012. Transcriptional activation of *Brassica napus* β-ketoacyl-ACP synthase II with an engineered zinc finger protein transcription factor. Plant Biotech J 10:783-791); and/or FATB (acyl-acyl carrier protein thioesterases; Bonaventure, G. (2003) Plant Cell. April 15 (4) 1020-33; PCT/EP2008/005551; PCT/US2010/061226) of a plant, such as a *Cruciferae* plant, for example a *Brassica* plant, including a plant of the *Brassica napus*, *Brassica juncea*, or *Brassica rapa* species. In one embodiment, the plant is an oilseed crop, such as flax (*Linum* sp.), rapeseed (*Brassica* sp.), soybean (*Glycine* sp.), sunflower (*Helianthus* sp.); cotton (*Gossypium* sp.), corn (*Zea mays*), olive (*Olea* sp.), safflower (*Carthamus* sp.), cocoa (*Theobroma cacoa*), peanut (*Arachis* sp.), hemp, oil palm, coconuts, groundnuts, sesame seed, castor bean, *lesquerella*, tallow tree, shea nuts, poppy seed, and/or jojoba seeds. Thus, provided herein are genes and plants, such as *Brassica* plants; that include modified alleles of, for example FatA1, FatA2, Kas2, Kas2 and/or FatB, that result in the production of the protein encoded by the gene to have reduced activity or no activity (as compared to wild type FatA1, FatA2, Kas2; Kas2 and/or FatB) or results in little to no protein product being produced.

For example, through use of a targeted/designed meganuclease and endogenous repair mechanisms, an insertion, substitution or deletion mutation can be created in any one of the genes described herein. A deletion mutation can be from 1 nucleotide to 400 plus nucleotides in length, including for example, 1, 2, 3, 4, 5, 6, 7, 8, 9, 10, 11, 12, 13, 14, 15, 16, 17, 18, 19, 20, 21, 22; 23, 24, 25, 26, 27, 28, 29, 30; 31, 32, 33, 34, 35, 36, 37, 38, 39, 40, 41; 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87; 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118; 119, 120; 121, 122; 123, 124; 125, 126, 127, 128, 129, 130, 131, 132, 133, 134, 135, 136, 137, 138, 139, 140, 141, 142, 143, 144, 145, 146, 147, 148, 149, 150, 151, 152, 153; 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317; 318, 319; 320, 321; 322, 323, 324, 325, 326, 327, 328, 329, 330, 331, 332, 333, 334, 335, 336, 337, 338, 339, 340, 341, 342, 342, 344, 345, 346, 347, 348, 349, 350, 351, 352; 353, 354; 355, 356; 357, 358; 359, 360, 361, 362, 363, 364, 365, 366, 367, 368, 369, 370, 371, 372, 373, 374, 375, 376, 377, 378, 379, 380, 381, 382, 383, 384, 385, 386, 387; 388, 389; 390, 391; 392, 393; 394, 395, 396, 397; 398, 399, 400 and so on (and any range encompassing such numbers or the entire gene). Such deletions can result in little to no expression of the gene (RNA and/or protein) and if protein is expressed from the gene, it will have no or reduced activity as compared to a wild type gene.

The engineered nuclease is provided to plants or plant tissues via conventional methods (e.g., DNA coding for engineered nuclease is inserted into a plasmid (generally operably linked components comprising a promoter sequence, engineered nuclease, terminator (stop) sequence and optionally an antibiotic resistance gene)) which is then introduced into the plant cells by any method available to the art, including for example into bacteria, such as *Agrobacterium tumefaciens*, but also by direct DNA transfer methods. Various methods for DNA delivery into cells/tissues (intact plant cells or partially degraded tissues or plant cells) are known in the art, and include electroporation as illustrated in U.S. Pat. No. 5,384,253; microprojectile bombardment (biolistics) as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6; 384; 301; protoplast transformation as illustrated in U.S. Pat. No. 5,508,184, electroporation, chemically-assisted transformation, liposome-mediated transformation (see, e.g., A. Deshayes, et al. (1985) EMBO J. 4:2731-7.), carbon fiber, silicon carbide fiber or aluminum borate fiber (generally termed whiskers) (see, e.g., J. Brisibe, Exp. Bot. 51 (343): 187-196 (2000); Dunwell (1999) Methods Mol. Biol. 111:375-82; and U.S. Pat. No. 5,464,765), microinjection (see, e.g., Reich, of al. (1986) Biotechnology 4: 1001-1004) and viral-mediated transformation (see, e.g., S. B. Gelvin, (2005) Nat Biotechnol. 23: 684-5, WO 90/12107, WO 03/052108 and WO 2005/098004), bombardment of plant cells with heterologous foreign DNA adhered to particles, ballistic particle acceleration, aerosol beam transformation (U.S. Patent Application No. 20010026941; U.S. Pat. No. 4,945,050; International Publication No. WO 91/00915; U.S. Patent Application No. 2002015066, WO 01/038514; all incorporated herein by reference), Led transformation, PEG transformation, and various other non-particle direct-mediated methods to transfer DNA. As used herein "direct DNA transfer" is any method of DNA introduction into plant cells which does not involve the use of natural *Agrobacterium* spp. and which is capable of introducing DNA into plant cells.

It will also be clear that the terms used to describe the method such as "introduction of a DNA" as well as "regeneration of a plant from the cell" do not imply that such DNA necessarily needs to be introduced by transformation techniques. Indeed, it will be immediately clear to the person skilled in the art that the DNA molecule of interest may also be introduced by breeding or crossing techniques from one plant to another. Thus, "introducing" in connection with the present application relate to the placing of genetic information in a plant cell or plant by any known means. This can be effected by any method known in the art for transforming RNA or DNA into plant cells, tissues, protoplasts or whole plants or by introgressing said RNA or DNA into plants as described below.

In the case of introducing DNA into a plant, plant tissue or pant cell(s) in which the mutation is desired (e.g., canola plant or plant tissue; including, for example, several varieties of the Brassicaceae plants, including for example, *Brassica napus, Brassica rapa, B. campestris* or *Brassica juncea* and mutated *Brassica* plants) via *Agrobacterium tumefaciens*, the plant, plant tissues, or plant cell(s) is exposed to the bacteria carrying the engineered nuclease. For example, the plant can be dipped in a solution comprising the bacterium or disks can be punched out from a plant leaf (or other plant tissue, such as the stems, can be used) and incubated with a culture of plasmid-containing *A. tumefaciens*. The disks/plant tissue are then placed under conditions to generate callus in the presence of antibiotic. Only those plant cells/tissue that have DNA from the plasmid (the resistance gene) will have antibiotic resistance. The conditions therefore select for the plant cells/tissue by killing those that do not contain plasmid DNA. After resistant callus is selected, they are transferred to medium that induces growth of shoots, where they grow roots, and then to soil to grow into mature plants.

Plants (offspring) are then selected for those which have a mutation in the desired gene (e.g.; such as those listed above). The selection process can look for altered size in the gene of interest and/or protein activity (protein normally produced by the gene of interest), as well as antibiotic resistance (an extra piece of DNA that was included in the plasmid inserted into the bacteria that provides for resistance to a specific antibiotic) or by sequence. Those plants with reduced to no activity in the desired gene (expression of RNA and/or protein), as compared to plants that were not exposed to the engineered nuclease (with identical starting backgrounds), are of particular interest. If the bacteria inserted any foreign DNA into the plant, these plants can be further bred until such DNA is no longer part of the mutated plant. The plants can also be bred so that they are homozygous for the mutation (e.g., deletion).

Also provided is a method crossing one or more first parent plants that contain a mutant allele at one or more loci of FatA1, FatA2, FatB, Kas2, and/or Kas3 and one or more second parent plants that contain a mutant allele at a different locus of FatA1, FatA2, FatB, Kas2, and/or Kas3, wherein each mutant allele results in the production of a polypeptide having reduced activity (or no activity) relative to a corresponding wild-type (or a gene that was not mutated as described herein) FatA1, FatA2, FatB, Kas2, and/or Kas3 polypeptide (or no polypeptide is produced at all); and selecting progeny plants having mutants alleles at two or more different loci thereby obtaining a desired plant.

Plant Products

Oils obtained from such plants, such as *Brassica* plants (canola oil), can have low or no saturated fatty acids and an altered oleic acid content as compared to a plant that was not mutated as described herein (identical genetic background to plant prior to exposure to an engineered nuclease). Oil content in the seeds can be determined by methods known to those of skill in the art.

In another aspect, a method of producing an oil is provided. The method includes crushing seeds produced from at least one *Brassica* plant described herein; and extracting oil from the crushed seeds. Such oils can be used in food compositions, spray coatings for food, and/or for frying applications (such as frying food, so as to produce fried foods such as snack chips (e.g., corn or potato chips), French fries, or other quick serve foods).

The invention will be further described in the following examples, which do not limit the scope of the invention described in the claims.

EXAMPLES

Example 1

Mutation of FatA1 with Use of a Meganuclease

Using a meganuclease specific for FatA1 (the expression of the desired meganuclease in a canola plant cell causes specific breaks in FatA1 DNA in the plant genome; repair of which leads to deletions, insertions and/or base pair changes), several canola plants with deletions in Fat1A were generated (ranging from 1 to 350 base pair deletions). This resulted in phenotypes with a decrease in C18:0 saturated fat production from about 7% to about 38%, with a reduction in combined C18:0/C20:0/C22:0/C24:0 from about 6% to about 33%, as compared to plants with an identical genetic background to the plant prior to exposure to an engineered nuclease.

Thus targeted mutation of Fat1A resulted in a significant and unexpected decrease in saturated fat production.

Example 2

FatA1 Mutation and Analysis

In the Tables provided below, the fatty acids are referred to by the length of the carbon chain and number of double bonds within the chain. For example, C14:0 refers to myristic acid; C16:0 refers to palmitic acid; C18:0 refers to stearic acid; C18:1 refers to oleic acid; C18:2 refers to linoleic acid; C18:3 refers to ALA; C20:0 refers to archidic acid; C20:1 refers to eicosenoic acid; C22:0 refers to behenic acid; C22:1 refers to erucic acid; C24:0 refers to lignoceric acid; and C24:1 refers to nervonic acid. "Total Sats" refers to the total of C14:0, C16:0, C18:0, C20:0, C22:0, and C24:0. Representative fatty acid profiles are provided for each of the specified samples.

Unless otherwise indicated, all percentages refer to fatty acid % based on total fatty acids (i.e., fatty acid moieties) in the oil.

Figure 5C:
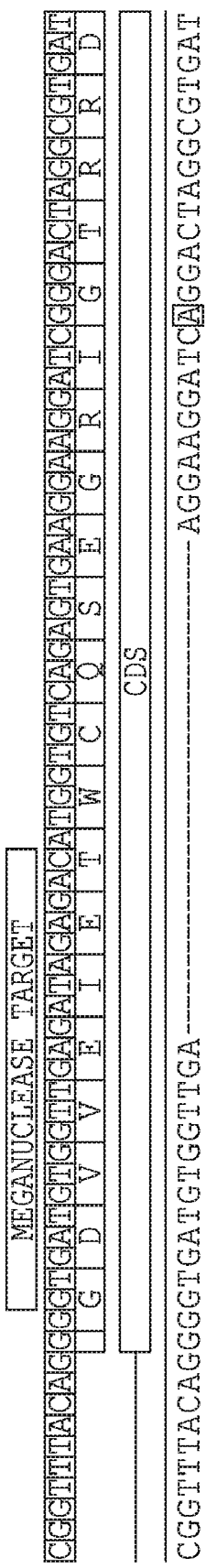

*Brassica* plants with lower saturated fatty acid were obtained by subjecting cells of *Brassica* plants to engineered meganucleases, followed by analysis of sequence (FIGS. 1-5) and saturated fatty acid production (Tables 1 and 2).

The average results of saturated fatty acid production in said mutant plant lines is presented in Tables 1 (IMC201 background) and Table 2 (Cargill background), showing mutated plant lines, prepared by the methods described herein having a reduction of saturated fatty acid 18:0 (stearic acid) of about 9% to about 34%, a reduction in 18/20/22/24 saturated fatty acids combined of about 5% to about 37%, and a reduction in total saturated fatty acids of about 6% to about 14%. "WE" indicates average results for non-mutated (e.g., wild-type allele(s)) plants of the identical genetic background.

TABLE 1

| Sample | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| Mutant (IMC201) | 1.84 | 23% | 0.82 | 0.53 | 0.34 | 3.54 | 21% | 8.02 | 11% |
| WT (IMC201) | 2.39 | | 1.04 | 0.65 | 0.38 | 4.46 | | 8.97 | |

TABLE 2

| Sample | C18:0 | % reduction C18:0 | C20:0 | C22:0 | C24:0 | Total Sats 18/20/22/24 | % reduction 18/20/22/24 | Total Sats | % reduction total sats |
|---|---|---|---|---|---|---|---|---|---|
| Mutant (Cargill) | 1.08 | 28% | 0.37 | 0.13 | 0.13 | 1.71 | 26% | 5.30 | 10% |
| WT (Cargill) | 1.49 | | 0.48 | 0.14 | 0.20 | 2.31 | | 5.90 | |

BIBLIOGRAPHY

D'Halluin et al. 2013. Targeted molecular trait stacking in cotton through targeted double-strand break induction. Plant Biotech J 11:933-41.

Djukanovic et al. 2013. Male-sterile maize plants produced by targeted mutagenesis of the cytochrome P450-like gene (MS26) using a re-designed I-CreI homing endonuclease. The Plant Journal 76:888-99.

Gao et al. 2010. Heritable targeted mutagenesis in maize using a designed endonuclease. The Plant Journal 61:176-187.

Honig et al. 2015. Transient expression of virally delivered meganuclease in planta generates inherited genomic deletions. Mol Plant 8:1292-4.

Puchta & Fauser. 2014. Synthetic nucleases for genome engineering in plants: prospects for a bright future. The Plant Journal 78:727-741.

Sprink et al. 2015. Plant genome editing by novel tools: TALEN and other sequence specific nucleases. Current Opinion in Biotech 32:47-53.

Tzfira et al. 2012. Genome modifications in plant cells by custom-made restriction enzymes. Plant Biotech Journal 10:373-389.

All patents, patent applications, accession numbers and publications cited herein are incorporated herein by reference in their entirety.

What is claimed is:

1. A method to mutate the genome of a *Brassica* plant cell at a target site comprising:
   a) inducing a double stranded DNA break at said target site in the genome of said plant cell, said double stranded break being induced by the introduction to said cell of a double stranded DNA break inducing (DSBI) enzyme which recognizes a recognition sequence at said target site in FatA1 gene of SEQ ID NO: 2, SEQ ID NO: 9, SEQ ID NO: 13, SEQ ID NO: 18 or a sequence at least 95% identical thereto; and
   b) selecting a plant cell wherein said double stranded DNA break has been repaired resulting in a deletion in the genome, wherein the deletion is in FatA1 of SEQ ID NO: 2, SEQ ID NO: 9, SEQ ID NO: 13, SEQ ID NO: 18 or a sequence at least 95% identical thereto.

2. The method of claim 1, wherein the method further comprises regenerating said plant cell(s) of b) into a plant.

3. A *Brassica* plant cell comprising a mutation at a target site of the genome obtained by the method of claim 1.

4. A *Brassica* plant, plant part, seed or propagating material thereof comprising a mutation at a target site of the genome comprising the plant cell of claim 3.

5. A method to produce a *Brassica* plant with reduced saturated fatty acids comprising:
   a) inducing a double stranded DNA break at a target site in the genome of a plant cell, said double stranded break being induced by the introduction to a plant cell of a double stranded DNA break inducing (DSBI) enzyme which recognizes a recognition sequence at said target site in FatA1 gene of SEQ ID NO: 2, SEQ ID NO: 9, SEQ ID NO: 13, SEQ ID NO: 18 or a sequence at least 95% identical thereto; and
   b) selecting a plant cell wherein said double stranded DNA break has been repaired resulting in a deletion in the genome, wherein the deletion is in FatA1 of SEQ ID NO: 2, SEQ ID NO: 9, SEQ ID NO: 13, SEQ ID NO: 18 or a sequence at least 95% identical thereto; and
   c) regenerating said plant cell(s) of b) into a plant;
   wherein said mutation results in reduced production of saturated fatty acids by said plant as compared to a control plant of identical genetic background that has not been mutated by said DSBI and repair.

6. The method of claim 1, wherein the DSBI enzyme is a single chain meganuclease or a pair of meganucleases which recognizes or recognize in concert a site and induces or induce said double strand break.

7. The method of claim 2, wherein the method further comprises crossing said plant with another plant.

8. A *Brassica* plant, plant part, seed or propagating material thereof comprising a mutation at a target site of the genome obtained by the method of claim 2.

9. The method of claim 1, wherein the *Brassica* plant is *Brassica napus*.

10. The method of claim 1, wherein one or both FatA1 alleles on N3, N7, N13 and/or N17 are mutated.

11. The method of claim 10, wherein one or both FatA1 alleles on N13 and/or N17 are mutated.

12. The method of claim 11, wherein one or both FatA1 alleles on N13 are mutated.

13. The method of claim 10, wherein one or both FatA1 alleles on N3, N7 and/or N13 are mutated.

14. The method of claim 13, wherein one or both FatA1 alleles on N7 are mutated.

15. The method of claim 2, wherein the plant yields a reduction of stearic acid (18:0) of about 9% to about 35% as compared to a non-mutated plant of identical genetic background.

16. The method of claim 2, wherein the plant yields an overall reduction in total saturated fatty acids of about 5% to about 15%.

* * * * *